United States Patent [19]

Franco

[11] Patent Number: 5,279,817
[45] Date of Patent: Jan. 18, 1994

[54] SUNTANNING OIL FORMULATION CONTAINING ANNATTO

[76] Inventor: Ricardo Franco, 300 S. Calle El Segundo, Apt. 118, Palm Springs, Calif. 92262

[21] Appl. No.: 955,933

[22] Filed: Oct. 2, 1992

[51] Int. Cl.⁵ .............. A61K 7/42; A61K 35/78
[52] U.S. Cl. ..................... 424/59; 424/195.1
[58] Field of Search .......... 424/78.03, 401, 195.1, 424/59

[56] References Cited

U.S. PATENT DOCUMENTS

| | | | |
|---|---|---|---|
| 4,368,187 | 1/1983 | Flom | 514/846 |
| 4,372,944 | 2/1983 | Herrold | 514/847 |
| 4,386,067 | 5/1983 | Guillon | 514/182 |
| 4,732,759 | 3/1988 | Shibanai | 514/725 |
| 5,032,382 | 5/1991 | Grollier | 514/937 |

*Primary Examiner*—Thurman K. Page
*Assistant Examiner*—Sally Gardner
*Attorney, Agent, or Firm*—Woodard, Emhardt, Naughton, Moriarty & McNett

[57] ABSTRACT

It has been discovered that annatto oil is a highly effective cosmetic enhancement for suntanning. When annatto is added to the formulation of a suntan oil, preferably with other naturally occurring oils, the wearer receives a suntan that is cosmetically more desirable than that attained with formulations that do not contain annatto. A preferred formulation is disclosed herein that is over 99.9% composed of naturally occurring ingredients.

1 Claim, No Drawings

SUNTANNING OIL FORMULATION CONTAINING ANNATTO

BACKGROUND OF THE INVENTION

This invention pertains to suntan oil formulations and more particularly to suntan oil formulations that contain a cosmetic enhancement.

It is well known that the cosmetically desirable effect of suntanning the human skin is due to radiation exposure. Specifically, the required rays reside in the ultraviolet range of the electromagnetic spectrum at a wavelength from about 3,150 to about 3,650 angstroms. Accordingly, a large number of commercial suntanning products are presently marketed which are intended to accentuate this skin darkening process. Such products generally work in two fashions. A first is to increase the skin's exposure to ultraviolet rays by enabling the skin to reside longer in the ultraviolet wave source. A second is to offer cosmetic aids in the formulation that enhance the existing tan by altering the tanned skin's hue. Of these numerous commercially prepared products, many use artificially synthesized compounds to pursue their goal.

However, a substantial number of persons do not desire to use formulations containing artificially synthesized chemical compounds and would prefer to use a suntan product containing naturally occurring substances. While some naturally occurring substances such as lanolin, peanut oil, sesame oil, and petrolatum have been disclosed as being suitable for use as a suntan oil, such naturally occurring materials do not generally contain cosmetic aids acceptable to the person desiring only naturally occurring compounds. Another problem associated with such cosmetic aids currently in use is that they do not successfully alter the existing tan's hue to a quality level that is acceptable to the wearer.

SUMMARY OF INVENTION

It has been discovered that annatto oil is a highly effective cosmetic enhancement for suntanning. When annatto is added to the formulation of a suntan oil, preferably with other naturally occurring oils, the wearer receives a suntan that is cosmetically more desirable than that attained with formulations that do not contain annatto. Additionally, the wearer can take comfort in the fact that the preferred formulation disclosed herein is over 99.9% composed of naturally occurring ingredients.

An object of this invention is to provide a suntan oil that offers superior performance in assisting a user to obtain an attractive suntan. A further object of this invention is to provide a suntan oil that contains a cosmetic enhancement to supplement the appearance of a user's existing tan. Still, a further objective of this invention is to provide a suntan oil with naturally existing compounds as cosmetic enhancements.

DESCRIPTION OF A PREFERRED EMBODIMENT

Annatto is a vegetable dye that is derived from the seed of Bixa Orellana. Bixa Orellana is known to grow in South America, the West Indies, and India. The annatto oil obtained therefrom is also known as arnato, achiote, bija, or achotte. The oil is obtained from the seed by conventional expression and solvent extraction techniques using a variety of solvents such as hexane, ether, and the like. Such seed-oil extraction techniques are common and therefore are outside the scope of this invention and do not provide any limitation thereof.

According to the present invention, it has been discovered that use of annatto oil in a suntan formulation is highly successful to enhance the human skin tanning process. It is not known whether annatto affects the manner in which the human body tans or cosmetically alters an existing tan's hue, or it may be a combination of both. But what is known is that the annatto oil's presence alters the suntanned skin's hue to a degree which is more desirable by many over the hue provided by most commercially available suntanning preparations.

Further disclosed herein is a description of ingredients and their formulation as a unique suntan oil. The critical distinction of this invention over commercially available products is the inclusion of annatto. Heretofore, the effect annatto has on the tanning process of the human skin has not been recognized.

The following description of ingredients is offered to aid the practitioner. All are commercially available and do not require any special preparation before use. Where seed extracts are mentioned, it must be understood that seed-oil extraction processes are commonplace and, as previously mentioned, are outside the scope of this invention. Any explanation of seed-oil origin is offered to assure that it is the actual oil obtained from the plant that is used.

As used herein, the term "white mineral oil" can be any colorless to slightly yellow, odorless, tasteless, liquid petrolatum. An example of such an oil is mineral oil no. 11252, sold under the trade name "DRAKEOL ®", sold by the Pennsylvania Refining Company.

The formulation disclosed herein requires naturally existing oil extracts. Such oils have commercial sources and thus are readily available. Therefore as used herein:

(b) The term "sesame oil" is that fatty oil which is obtained from sesame seeds and is also known as Benne oil or Teel oil.

(c) The term "safflower oil" is that fatty oil which is obtained from safflower seeds.

(d) The term "avocado oil" is that fatty oil which is obtained from the seed of the fruit of an avocado tree.

(e) The term "sweet almond oil" is that fatty oil obtained from kernels of sweet almonds.

(f) The term "apricot kernel oil" is that fatty oil obtained from kernels of apricots.

(g) The term "grape seed oil" is that fatty oil obtained from kernels of grapes.

(h) The term "kukui nut oil" is that fatty oil obtained from the nuts of a kukui tree. The substance is also known as candlenut oil.

(i) The term "wheat germ oil" is that fatty oil obtained from wheat germ.

(j) The term "cod-liver oil" is that fatty oil obtained from the livers of codfish and is also known as morrhua oil.

As used herein, the term "COVI-OX ®" T-50 (generically known as vitamin E) is the trade name of a compound with commercial sources and thus is readily available.

As used herein, the term "annatto oil" is that fatty oil previously described but for repetition purposes is obtained from the seeds of Bixa Orellana and is also known as arnato, achiote, bija, and achotte.

As used herein, the term "mango fragrance" is a compound used to give the formulation a pleasing aroma. The fragrance has many commercial sources and therefore is readily available.

As used herein, the term "antioxidant" is any food grade antioxidant containing one or more of the following ingredients: butylated hydroxyanisole, butylated hydroxytoluene, or propyl gallate, di-tert-butyl-p-cresol, and with or without citric acid or phosphoric acid. The antioxidant may or may not be supplied in a solvent such as propylene glycol. An example of an acceptable antioxidant is "TENOX ® BHA" serial no. 17203, a trademark of the Tennessee Eastman Company.

A preferred embodiment of the invention disclosed herein requires combining the aforementioned materials in the respective proportions as described in TABLE 1.

TABLE 1

| Ingredient | Percentage by Weight | |
|---|---|---|
| | preferred | (allowable range) |
| White Mineral Oil | 54.93 | (52 to 57) |
| Sesame Oil | 15 | (13 to 17) |
| Safflower Oil | 10 | (8 to 12) |
| Avocado Oil | 3 | (2 to 4) |
| Sweet Almond Oil | 3 | (2 to 4) |
| Apricot Kernel Oil | 5 | (4 to 6) |
| Grape Seed Oil | 6 | (5 to 7) |
| Kukui Nut Oil | 0.10 | (0.08 to 0.12) |
| Wheat Germ Oil | 2 | (1 to 3) |
| Cod Liver Oil | 0.5 | (0.4 to 0.6) |
| COVI-OX ® T-50 (Vitamin E) | 0.010 | (0.008 to 0.012) |
| Annatto Oil | 0.25 | (0.1 to 1.0) |
| Mango Fragrance | 0.2 | (0.1 to 0.4) |
| Antioxidant | 0.01 | (0.001 to 0.02) |

The ingredients as proportioned in TABLE 1 can be combined in any order in any container suitable to hold such organic compounds. The ingredients are preferably combined at room temperature and preferably the total volume prepared is that which allows for adequate mixing of the ingredients. Such volume is defined by the container and mixing apparatus used. Such mixing containers, mixing apparatuses, and corresponding requisite volumes are readily known to those in the art.

After all the ingredients are combined, they are thoroughly mixed until the ingredients are uniformly admixed throughout the entire volume. Upon completion, the formulation is ready for use or bottling for later use using conventional bottling techniques.

The formulation is applied to the human skin before, during, or after exposure to a natural or artificial ultraviolet ray source. The formulation can be wiped on the body as a lotion or sprayed on the body as a mist. Preferably, the formulation is applied before exposure and at least about once every hour during exposure. Most preferably, the oil is applied once before exposure and at least every thirty minutes while exposed. It must be understood that the aforementioned frequencies are approximations and that the frequency to which the formulation disclosed herein should be applied will vary inversely with an individual's melanin production rate at the skin's surface. That is, fairer complexions may require frequencies at least as often as every fifteen minutes and darker complexions may require use at about ninety minute intervals. Furthermore, the degree of tanning desired and the degree of cosmetic enhancement desired will vary directly with the total amount formulation used.

What is claimed is:

1. A composition of matter suitable as a suntan oil, consisting essentially of:

| | | |
|---|---|---|
| (a) | White Mineral Oil | from 52 to 57 wt. % |
| (b) | Sesame Oil | from 13 to 17 wt. % |
| (c) | Safflower Oil | from 8 to 12 wt. % |
| (d) | Avocado oil | from 2 to 4 wt. % |
| (e) | Sweet Almond Oil | from 2 to 4 wt. % |
| (f) | Apricot Kernel Oil | from 4 to 6 wt. % |
| (g) | Grape Seed Oil | from 5 to 7 wt. % |
| (h) | Kukui Nut Oil | from 0.08 to 0.12 wt. % |
| (i) | Wheat Germ Oil | from 1 to 3 wt. % |
| (j) | Cod Liver Oil | from 0.4 to 0.6 wt % |
| (i) | Vitamin E | from 0.008 to 0.012 wt. % |
| (j) | Annatto Oil | from 0.1 to 1.0 wt. % |
| (k) | Mango Fragrance | from 0.1 to 0.4 wt. % and |
| (l) | Antioxidant | from 0.001 to 0.02 wt. %; | wherein the total percentage of ingredients (a) thru (l) does not exceed 100 wt. % and wherein said Antioxidant is a food grade antioxidant containing one or more ingredients from the group consisting of butylated hydroxyanisole, butylated hydroxytoluene, propyl gallate, di-tert-butyl-p-cresol.

* * * * *